United States Patent [19]

Iizuka et al.

[11] 4,226,878
[45] Oct. 7, 1980

[54] IMIDAZOLE DERIVATIVE

[75] Inventors: Kinji Iizuka; Kenji Akahane; Denichi Momose; Yukio Kamijo, all of Matsumoto; Yukiyoshi Ajisawa, Okaya, all of Japan

[73] Assignees: Kissei Pharmaceutical Co., Ltd., Matsumoto; Ono Pharmaceutical Co., Ltd., Osaka, both of Japan

[21] Appl. No.: 48,112

[22] Filed: Jun. 13, 1979

[30] Foreign Application Priority Data

Jun. 13, 1978 [JP] Japan .................... 53-71273

[51] Int. Cl.³ .................. C07D 233/60; A61K 31/415
[52] U.S. Cl. .................. 424/273 R; 548/335
[58] Field of Search .................. 548/341, 335; 424/273 R

[56] References Cited

U.S. PATENT DOCUMENTS 3,531,494   9/1970   Adolphi et al. .................. 548/341

FOREIGN PATENT DOCUMENTS 1119334   7/1968   United Kingdom .................. 548/335

Primary Examiner—John D. Randolph
Assistant Examiner—Robert T. Bond

Attorney, Agent, or Firm—Sughrue, Rothwell, Mion, Zinn and Macpeak

[57] ABSTRACT

Novel imidazole derivatives of the general formula (I):

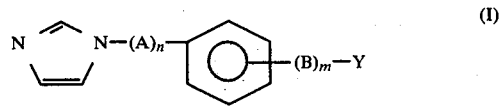

wherein Y is a carboxyl group, an alkoxycarbonyl group, a cyano group, a hydroxymethyl group, an aminomethyl group, a formyl group or a carbamoyl group, and A and B, which may be the same or different, each is a straight- or branched-chain alkylene or alkenylene group, and n and m, which may be the same or different, each is zero or 1, with the proviso that when A is methylene group or n is zero, m is 1; and pharmaceutically acceptable salts thereof. These compounds have a strong inhibitory effect on thromboxane synthetase from rabbit platelet microsomes, and are useful as therapeutically active agents for the treatment of inflammation, hypertension, thrombus, cerebral apoplexy and asthma.

22 Claims, No Drawings

IMIDAZOLE DERIVATIVE

BACKGROUND OF THE INVENTION

1. Field of the Invention

This invention relates to novel imidazole derivatives. More particularly, this invention relates to N-(ω-substituted alkyl-phenylalkyl), N-(ω-substituted alkylphenyl) and N-(nucleus substituted phenylalkyl) imidazoles possessing an extremely strong inhibitory action for thromboxane synthetase and inhibiting the biosynthesis of thromoboxane $A_2$.

2. Description of the Prior Art

Up to now, of the compounds having an imidazole skeleton, it has been reported that imidazole, 1-alkylimidazoles, 1-benzylimidazole, 1-(2-isopropylphenyl)imidazole and their analogue possess an inhibitory action for thromboxane synthetase [Prostaglandins, Vol. 13, No. 4, 611-, (1977), BIOCHEMICAL AND BIOPHYSICAL RESEARCH COMMUNICATIONS, Vol. 80, No. 1, 236- (1978)]. However, since imidazole and 1-lower alkylimidazoles of those compounds above show only very weak inhibitory effect, these compounds are hardly applicable as practically effective medicines. On the other hand, 1-benzylimidazole, 1-(2-isopropylphenyl)imidazole, 1-higher alkylimidazoles such as 1-nonylimidazole and 1-decylimidazole, and their analogue show a strong inhibitory effect compared with imidazole and 1-lower alkylimidazoles, but the inhibitory potency of these compounds is yet far from satisfactory one as therapeutically active agents. And the action of these compounds is not a specific inhibitory action for thromboxane synthetase because of possessing both inhibitory actions for thromboxane synthetase and cyclooxygenase. Furthermore, in the case of 1-(2-isopropylphenyl)imidazole, it is difficult to prepare this compound, so that the problem of industrial application remains still unsettled.

Meanwhile, many compounds which have an imidazole skeleton and which might be considered superficially to be similar to the compounds of this invention from a chemical structural standpoint have been reported, e.g., in *Monatsch Chem.* Vol. 108, No. 5, 1059-, (1977), *J. Med. Chem.* Vol. 18, No. 8, 833-, (1975), *J. Amer. Chem. Soc.* Vol. 79, 4922-, (1957), U.S. Pat. No. 3,541,109, French Pat. No. 7,779M, French Pat. No. 1,486,817, *Chemical Abstracts*, Vol. 71, 90645g, (1969), 83, 164069u, (1975), 88, 36814z, (1978), *J. Org. Chem.* Vol. 22, 1323-, (1975) British Pat. No. 1,148,103, etc. Although some of these compounds, especially 1-(6-methoxycarbonylhexyl) imidazole, show a inhibitory effect on thromboxane synthetase, but the inhibitory potency is not completely satisfactory as a practical medication, and the others do not show a inhibitory effect on thromboxane synthetase.

Therefore, research directed towards developing compounds possessing a much stronger and more specific inhibitory effect on thromboxane synthetase has been long demanded in the medical field.

As a result of extensive research and experimentation carried out for imidazole derivatives, it was found that such demand was satisfied with use of N-(ω-substituted alkylphenylalkyl), N-(ω-substituted alkylphenyl) and N-(nucleus-substituted phenylalkyl)imidazole. The imidazole derivatives of this invention possess a strong and specific inhibitory effect on thromboxane synthetase and are useful as therapeutically active agents for the treatment of inflammation, hypertension, thrombus, cerebral apoplexy and asthma.

SUMMARY OF THE INVENTION

Accordingly, an object of this invention is to provide compounds which exhibit a strong and specific inhibitory effect on thromboxane synthetase and which are therapeutically useful.

Another object of this invention is to provide new imidazole derivatives possessing a pharmacological effect.

Still another object of this invention is to provide N-(ω-substituted alkylphenylalkyl), N-(ω-substituted alkylphenyl) and N-(nucleus-substituted phenylalkyl)imidazoles or the pharmaceutically acceptable salts thereof.

Yet another object of this invention is to provide pharmaceutical compositions comprising N-(ω-substituted alkylphenylalkyl), N-(ω-substituted alkylphenyl) and N-(nucleus-substituted phenylalkyl) imidazoles or the pharmaceutically acceptable salts thereof.

A further object of this invention is to provide methods for the treatment of the diseases such as inflammation, hypertension, thrombus, cerebral apoplexy and asthma, using N-(ω-substituted alkylphenylalkyl), N-(ω-substituted alkylphenyl) and N-(nucleus-substituted phenylalkyl)imidazoles or the pharmaceutically acceptable salts thereof.

Other objects, features and advantages of this invention will become more apparent from the following description of the invention.

DETAILED DESCRIPTION OF THE INVENTION

The present invention provides imidazole derivatives of the general formula (I):

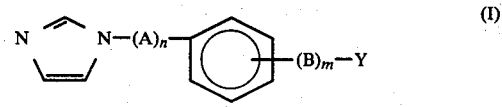

wherein Y is a carboxyl group, an alkoxycarbonyl group, a cyano group, a hydroxymethyl group, an aminomethyl group of the formula

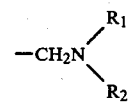

(wherein $R_1$ and $R_2$, which may be the same or different, each is a hydrogen atom or an alkyl group), a formyl group or a carbamoyl group of the formula

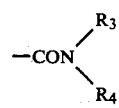

(wherein $R_3$ and $R_4$, which may be the same or different, each is a hydrogen atom or an alkyl group), and A and B, which may be the same or different, each is a straight- or branched-chain alkylene or alkenylene group, and n and m, which may be the same or different, each is zero or 1, with the proviso that when A is methylene group or n is zero, m is 1; and pharmaceutically acceptable salts thereof.

The term "alkyl" as used herein means a straight- or branched-chain alkyl group having 1 to 6 carbon atoms.

The term "alkoxycarbonyl" as used herein means a straight- or branched-chain alkoxycarbonyl group having 2 to 7 carbon atoms.

The term "alkylene" or "alkenylene" as used herein means a straight- or branched-chain alkylene or alkenylene group having 1 to 8 carbon atoms unless otherwise indicated.

The term "acid residual group" as used herein means a halogen atom or an acid residual group formed from an organic or inorganic sulfonic acid.

The imidazole derivatives of the general formula (I) of this invention exhibit an inhibitory action for thromboxane synthetase from rabbit platelet microsomes. That is, the imidazole derivatives of this invention inhibit conversion of PROSTAGLANDIN $H_2$ into THROMBOXANE $B_2$ via THROMBOXANE $A_2$ which is unstable intermediate, and which is known to induce irreversible platelet aggregation and to contract smooth muscle and particularly muscle of blood vessel. [*Nature*, Vol. 261, No. 6, 17-, (1976)]. These facts demonstrate that the imidazole derivatives of this invention inhibit the biosynthesis of thromboxane $A_2$, and are thus useful for the treatment of diseases caused by thromboxane $A_2$, such as inflammation, hypertension, thrombus, cerebral apoplexy and asthma.

The inhibitory action of the imidazole derivatives of this invention can be confirmed by determination of thromboxane $B_2$ produced by thromboxane synthetase from prostaglandin $H_2$ via thromboxane $A_2$. Furthermore, the inhibitory action of the imidazole derivatives of this invention can be confirmed by determination of the inhibitory effect on platelet aggregation caused by arachidonic acid (arachidonic acid is converted to prostaglandin $H_2$ by cyclooxygenase, and prostaglandin $H_2$ converted to thromboxane $B_2$ via thromboxane $A_2$ which is known to induce platelet aggregation as described above).

Further still, the inhibitory action of the imidazole derivatives of this invention can be confirmed by determination of the inhibitory effect on sudden deaths caused by arachidonic acid.

The imidazole derivatives of this invention are characterized by the presence of the side chain having benzene ring, which is attached at 1-position of imidazole skeleton, and which has a functional group at the ω-position of the side chain or on the benzene ring (in the case of m being zero), selected from the group consisting of a carboxyl group, an alkoxycarbonyl group, a cyano group, a hydroxymethyl group, an aminomethyl group, a formyl group and a carbamoyl group.

In the general formula (I) above, m is limited to 1 when A is methylene group or n is zero.

In the imidazole derivatives of this invention, the side chain and the species of the functional group at the ω-position of the side chain or on the benzene ring (in the case of m being zero) play an important role in providing the inhibitory effect. That is, in general, the potency of the inhibitory action for thromboxane synthetase becomes higher as the whole linear carbon number of A and B increases. To show significant inhibitory action for thromboxane synthetase, two or more carbon atoms are required in A and B all together.

On the other hand, as the functional group at ω-position of the side chain or on the benzene ring (in the case of m being zero), a carboxyl group, an alkoxycarbonyl group, a cyano group, a hydroxymethyl group, an aminomethyl group, a formyl group and a carbamoyl group can be employed in this invention. Of the functional groups at ω-position of the side chain or on the benzene ring (in the case of m being zero), a carboxyl group, an alkoxycarbonyl group, a carbamoyl group and a formyl group are preferred. In this invention, a carboxyl group and an alkoxycarbonyl group are the more preferred functional groups at ω-position of the side chain or on the benzene ring (in the case of m being zero), and a carboxyl group is the most preferred functional group at ω-position of the side chain or on the benzene ring (in the case of m being zero).

The position of substitution on the benzene ring may be in any of the o-, m- and p-positions, but m- and p-substituted compounds tend to have a stronger inhibitory effect on thromboxane synthetase compared with o-substituted compounds. In this invention, compounds carrying an alkyl group, especially methyl group, at α-position of the functional group of the side chain have a tendency to increase in the inhibitory effect.

In the general formula (I) above, A and B are a straight- or branched-chain alkylene or alkenylene group having 1 to 8 carbon atoms, and no significant difference is found in the inhibitory effect between the alkylene compounds and the alkenylene compounds.

Preferred examples of the imidazole derivatives of this invention include compounds wherein the aggregate number of the linear carbon atoms in A and B is 2, 3 or 4 and the functional group at ω-position of the side chain is a carboxyl group or an alkoxycarbonyl group. That is, p-(1-imidazolylmethyl)cinnamic acid, 3-[p-(1-imidazolylmethyl)phenyl]propionic acid, 4-[p-(1-imidazolylmethyl)phenyl]butyric acid, 4-[m-(1-imidazolyl) phenyl]butyric acid, p-[3-(1-imidazolyl)-1-propenyl]benzoic acid, p-[γ-(1-imidazolyl)propyl]benzoic acid, p-(1-imidazolylmethyl)-α-methylcinnamic acid, 5-[m-(1-imidazolyl)phenyl] pentanoic acid, 4-[p-(1-imidazolyl)phenyl]butyric acid, ethyl m-(1-imidazolylmethyl)cinnamate, ethyl 4-[m-(1-imidazolylmethyl)phenyl]butyrate, ethyl p-(1-imidazolyl)cinnamate, ethyl 4-[p-(1-imidazolyl)phenyl]butyrate, ethyl 4-[p-(1-imidazolylmethyl)phenyl]butyrate, ethyl o-(1-imidazolylmethyl)cinnamate, and ethyl 4-[m-(1-imidazolyl)phenyl]butyrate are preferred.

More preferred examples of the imidazole derivatives of this invention include wherein the aggregate number of the linear carbon atoms in A and B is 3 or 4 and the functional group at ω-position of the side chain is a carboxyl group or an alkoxycarbonyl group. That is, p-(1-imidazolylmethyl)-α-methylcinnamic acid, p-(1-imidazolylmethyl)cinnamic acid, p-[γ-(1-imidazolyl)-propyl]benzoic acid, 5-[m-(1-imidazolyl) phenyl]pentanoic acid and ethyl 5-[m-(1-imidazolyl)phenyl] pentanoate are more preferred.

Most preferred examples of the imidazole derivatives of this invention include wherein the aggregate number of the linear carbon atoms in A and B is 3 or 4 and the functional group at ω-position of the side chain is a carboxyl group. That is, p-(1-imidazolylmethyl)-α-methylcinnamic acid, p-(1-imidazolylmethyl)cinnamic acid, p-[γ-(1-imidazolyl)propyl] benzoic acid, 5-[m-(1-imidazolyl)phenyl]pentanoic acid are most preferred.

The imidazole derivatives of the general formula (I) of this invention can be prepared by the following procedures.

Of the imidazole derivatives of the general formula (I), for example, the compounds of the general formula (Ia)

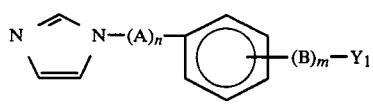 (Ia)

wherein $Y_1$ is a carboxyl group, an alkoxycarbonyl group or a cyano group, and A and B, which may be the same or different, each is a straight- or branched-chain alkylene or alkenylene group, and n and m, which may be the same or different, each is zero or 1, with the proviso that when A is methylene group or n is zero, m is 1, can be prepared by reacting imidazole of the formula (II):

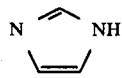 (II)

with a compound of the general formula (III):

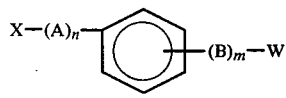 (III)

wherein X is an acid residual group, and W is an alkoxycarbonyl group or a cyano group and A, B, m and n have the same meanings as given above, and then if desired, hydrolyzing the resulting product to for a compound wherein $Y_1$ is a carboxyl group.

Of the imidazole derivatives of general formula (I), the compounds of the general formula (Ib):

 (Ib)

wherein A, B, m and n have the same meanings as given above, can be prepared by hydrogenating a compound of the general formula (Ia) wherein $Y_1$ is an alkoxycarbonyl group, using lithium aluminium hydride, etc.

Also, of the imidazole derivatives of the general formula (I), the compounds of the general formula (Ic):

 (Ic)

wherein A, B, m and n have the same meanings as given above, and $R_1$ and $R_2$, which may be the same or different, each is a hydrogen atom or an alkyl group, can be prepared by halogenating a compound of the general formula (Ib) above, using a halogenating agent such as thionyl chloride, etc., and then reacting the resulting compound with a compound of the general formula (IV):

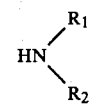 (IV)

wherein $R_1$ and $R_2$ have the same meanings as given above.

Still more, of the imidazole derivatives of the general formula (I), the compounds of the general formula (Id):

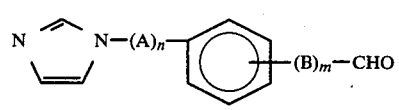 (Id)

wherein A, B, m and n have the same meanings as given above, can be prepared by hydrogenating a compound of the general formula (Ia) above wherein $Y_1$ is an alkoxycarbonyl group, using diisobutyl aluminium hydride, etc.

Furthermore, of the imidazole derivatives of the general formula (I), the compounds of the general formula (Ie):

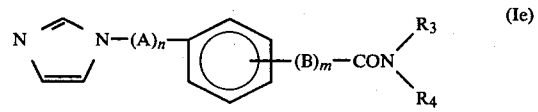 (Ie)

wherein $R_3$ and $R_4$, which may be the same or different, each is a hydrogen atom or an alkyl group, and A, B, m and n have the same meanings as given above, can be prepared by reacting a compound or a reactive functional derivative of the general formula (Ia) wherein $Y_1$ is a carboxyl group, with a compound of the general formula (IV'):

 (IV')

wherein $R_3$ and $R_4$ have the same meanings as given above, in the presence or absence of a condensing agent such as phosphorus oxychloride, etc.

The above-mentioned processes are well known in the art, and can easily be carried out according to the procedures described in the literature.

That is, the N-alkylation described above in the reaction of imidazole of the formula (II) with a compound of a general formula (III) can easily be carried out by dissolving imidazole in an inert organic solvent, e.g., benzene, tetrahydrofuran, dioxane, toluene, xylene, nitrobenzene, acetonitrile, N,N-dimethylformamide, ethanol, butanol, etc., adding a basic substance such as sodium carbonate, potassium carbonate, sodium hydride, sodium hydroxide, potassium hydroxide, a sodium alkoxide such as sodium methoxide, sodium ethoxide and the like, disopropylethylamine, pyridine, triethylamine, etc., in an equimolar amount to imidazole, and heating the mixture to about room temperature to about 200° C., for about 10 minutes to about 20 hours, subsequently, adding the compound of the general formula (III) in a proportion of about 1 to 0.9 mol per mole of imidazole to the reaction mixture, and then heating the resulting mixture to about 20° to about 200° C. for about 10 minutes to about 20 hours. The reaction mixture is concentrated under reduced pressure, the residue is recrystallized, distilled or column-chromatographed to obtain the desired product. And if desired, the resulting product is hydrolyzed in a usual manner in an aqueous solution of an acid or an alkali to obtain the acid-compound. In this process, the above reaction can be carried out preferably by using an adequate amount of a catalyst such as cuprous bromide, cuprous chloride, etc., and instead of using the basic substance, the reaction may be carried out by using imidazole in an excess amount, e.g., more than twice the molar amount of the compound of the general formula (III) above.

Furthermore, the N-alkylating reaction above can be carried out in the absence of any solvent, and can be carried out in the presence of a crown ether or a phase transfer catalyst such as tetrabutyl ammonium bromide, etc.

In the process of this invention, the imidazole used as starting material is well known and can easily be prepared according to methods disclosed in the literature. The compounds of the general formula (III) are known compounds and can also easily be prepared according to methods disclosed in the literature.

The above-described hydrogenation of the compound of the general formula (Ia) wherein $Y_1$ is an alkoxycarbonyl group to produce the compound of the general formula (Ib) can also be carried out according to well known methods. For example, a compound of the general formula (Ia) wherein $Y_1$ is an alkoxycarbonyl group may be dissolved in an inert organic solvent, e.g., diethyl ether, tetrahydrofuran, benzene, xylene, etc., and an adequate amount of lithium aluminium hydride is added to the solution, the mixture is stirred at room temperature or heated to about 30° to about 100° C., preferably about 50° to about 100° C., for about 1 to about 10 hours, preferably about 2 to 8 hours, and then the reaction mixture is treated in a usual manner and the object product can be obtained by recrystallization, distillation or column-chromatography.

The above-mentioned process for the production of the compound of the general formula (Ic) can be carried out according to the procedures known per se. That is, a compound of the general formula (Ib) is treated with a halogenating agent such as thionyl chloride in an inert organic solvent such as benzene, chloroform, etc., or in the absence of any solvent at about 30° to about 100° C., preferably about 50° to about 80° C., for an adequate period of time, and the reaction mixture is concentrated under reduced pressure to obtain the halogenated compound. A compound of the general formula (IV) above in a proportion of about 1 to 0.9 mol per mol of the compound of the general formula (Ib) and an adequate of a basic substance such as pyridine, triethylamine, etc., are added to an inert organic solvent such as benzene, chloroform, dichloromethane, etc., and the mixture is stirred on an ice-water bath, and then the halogenated compound above is added to the mixture. The mixture is heated at about 40° to about 80° C., for about 1 hour to 10 hours. The reaction mixture is concentrated under reduced pressure, the residue is recrystallized, distilled or column-chromatographed to obtain the compound of the general formula (Ic).

In the similarity, the above-described hydrogenation of the general formula (Ia) wherein $Y_1$ is an alkoxycarbonyl group, to produce the compound of the general formula (Id), may also be carried out by the method described in *J.Org. Chem.*, Vol. 31, 1447-, (1966). That is, the compound of the general formula (Ia) wherein $Y_1$ is an alkoxycarbonyl group, is dissolved in an inert organic solvent, e.g., chloroform, dichloromethane, hexane, toluene, etc., and the solution is cooled to about 0° to about −70° C., preferably about −50° to about −70° C., with stirring, then an adequate amount of diisobutyl aluminium hydride (a solution in hexane or toluene) is added to the solution, and the solution is stirred for about 10 minutes to about 6 hours, preferably about 30 minutes to about 2 hours, at about 0° to about −70° C., preferably about −50° to about −70° C. The reaction mixture is treated in a usual manner and the object product can be obtained by recrystallization, distillation or column-chromatography.

Furthermore, the above-described amidation of a compound of the general formula (Ia) wherein $Y_1$ is a carboxyl group, to produce the compounds of the general formula (Ie), can also be carried out by usual methods. That is, the compound of the general formula (Ia) wherein $Y_1$ is a carboxyl group, and the compound of the general formula (IV') in an equimolar amount to the compound of the general formula (Ia) are stirred at room temperature or at about 30° to about 150° C. for about 3 hours to 8 hours in an inert organic solvent, e.g., benzene, toluene, xylene, dioxane, etc., or in the absence of any solvent, in the presence or absence of an adequate amount of a condensing agent such as phosphorus oxychloride, etc., and then the reaction mixture is treated in usual methods, the object product can be obtained by recrystallization, distillation or column-chromatography. This amidation can also be carried out by using a reactive functional derivative of a compound of the general formula (Ia) wherein $Y_1$ is a carboxyl group, as a starting material. For example, in the case of using acid halide as a reactive functional derivative of the compound of the general formula (Ia) wherein $Y_1$ is a carboxyl group, the compound of the general formula (Ia) wherein $Y_1$ is a carboxyl group, is dissolved in an inert organic solvent, e.g., benzene, toluene, xylene, chloroform, dichloromethane, etc., and an adequate amount of thionyl chloride is added to the solution, then the mixture is heated for about 1 hour to about 3 hours at about 50° to about 80° C. The reaction mixture is concentrated under reduced pressure to obtain the acid chloride of the compound of the general formula (Ia) wherein $Y_1$ is a carboxyl group.

An amine compound of the general formula (IV') above in a proportion of about 1 to 0.9 mol per mol of the compound of the general formula (Ia) is dissolved in an inert organic solvent such as benzene, toluene, xylene, chloroform, dichloromethane, etc., and the solution is stirred on an ice-water bath, then the above acid chloride is added to the solution. The reaction mixture is heated to about 50° to about 100° C., preferably about 60° to about 80° C., for about 1 hour to about 5 hours, preferably about 2 hours to about 3 hours, and then the reaction mixture is concentrated under reduced pressure, the residue is recrystallized, distilled or column-chromatographed to obtain the desired product.

In this process, an acid halide, a mixed acid anhydride, an acid anhydride, an ester and a reaction product of said acid compound and carbodiimide can be employed as a reactive functional derivative of said acid compound.

Alternatively, in the compounds of the general formula (I), the compounds of the general formula (Ia')

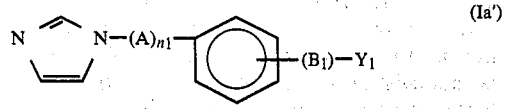

wherein $B_1$ is a straight- or branched-chain alkenylene group having 2 to 8 carbon atoms, and $n_1$ is zero or 1, and A and $Y_1$ have the same meanings as given above, can be prepared by treating in the Wittig reaction and compound of the general formula (V):

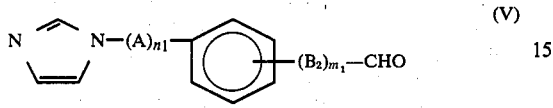

wherein $B_2$ is a straight- or branched-chain alkylene or alkenylene group having 1 to 7 carbon atoms, and $m_1$ is zero or 1, and A and $n_1$ have the same meanings as given above, with a compound of the general formula (VI):

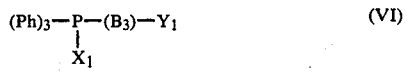

wherein $B_3$ is a straight- or branched-chain alkylene or alkenylene group having 1 to 7 carbon atoms, with the proviso that the aggregate number of carbon atoms in $B_2$ and $B_3$ is not more than 8, $X_1$ is a halogen atom, Ph is a phenyl group, $Y_1$ has the same meanings as given above; or a compound of the general formula (VI'):

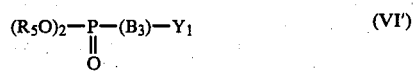

wherein $R_5$ is an alkyl group, $B_3$ and $Y_1$ have the same meanings as given above, and then if desired, hydrolyzing the resulting product to form a compound wherein $Y_1$ is a carboxyl group.

In this process, the compounds of the general formula (V) can be prepared according to a similar reaction manner of a compound of the general formula (III) with imidazole.

The above Wittig reaction can be carried out, for example, by a process wherein a compound of the general formula (V) is treated in an inert organic solvent such as diethyl ether, tetrahydrofuran, dioxane, benzene, hexane, dimethyl sulfoxide, etc., with a compound of the general formula (VI) or (VI') about 0° to about 100° C., preferably at room temperature to 80° C. The reaction mixture is treated in a usual manner, and the object product can be obtained by recrystallization or distillation or column-chromatography.

Of the compounds of the general formula (I), the compounds of the general formula (If):

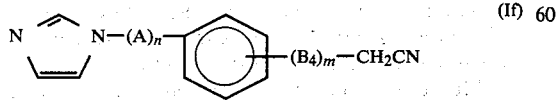

wherein $B_4$ is a straight- or branched-chain alkylene or alkenylene groups having 1 to 7 carbon atoms, A, n and m have the same meanings as given above, can also be prepared by halogenating the compound of the general formula (Ib) with a halogenating agent such as thionyl chloride in an inert organic solvent such as chloroform, benzene, etc., or in the absence of any solvent, for about 1 to about 3 hours at about 40° to about 80° C., and then reacting the resulting product with a cyanogenating agent such as sodium cyanide, potassium cyanide, etc., in an inert organic solvent such as acetone, dimethyl sulfoxide, etc., for about 1 hour to about 10 hours, preferably about 3 hours to about 5 hours, at about 30° to about 150° C., preferably about 40° to about 100° C.

Of the compounds of the general formula (I), the compounds of the general formula (Ig):

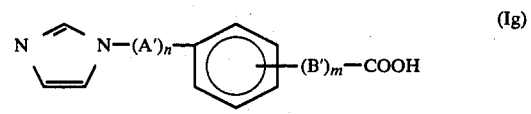

wherein A', B', which may be the same or different, each is a straight- or branched-chain alkylene group, n and m have the same meanings as given above, can also be prepared by following procedure. That is, the compounds of the general formula (Ig) can easily be prepared by reacting imidazole of the formula (II) above with a compound of the general formula (VII):

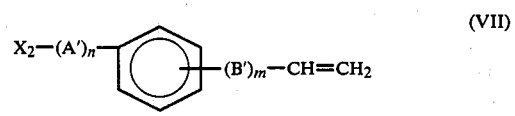

wherein $X_2$ is a halogen atom, A', B', n and m have the same meanings as given above, according to a similar reaction manner of the compound of the general formula (III) with imidazole of the formula (II); and then oxidating the resulting product using an oxidizing agent such as potassium permanganate, etc., in an inert organic solvent as benzene, etc., or in water, in the presence or absence of a crown ether, for about 1 hour to about 10 hours, preferably about 3 hours to about 5 hours, at room temperature to about 50° C., preferably room temperature.

Furthermore, in the compounds of the general formula (I), the compounds of the general formula (Ih):

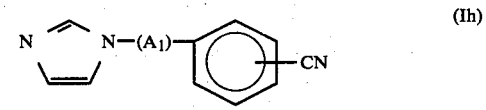

wherein $A_1$ is a straight- or branched-chain alkylene or alkenylene group having 2 to 8 carbon atoms, can be prepared by reacting a compound of the general formula (VIII):

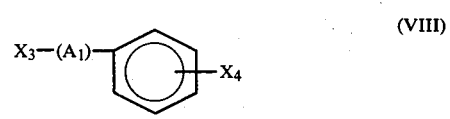

wherein $X_3$ and $X_4$, which may be the same or different, each is a halogen atom, $A_1$ has the same meanings as given above, according to similar reaction manner of a compound of the general formula (III) with imidazole above, and then reacting the resulting product with a cyanating agent such as cuprous cyanide, etc., in an inert organic solvent such as N,N-dimethylformamide, etc., for several times at about 80° to about 150° C.

In this invention, a compound of the general formula (I) wherein A and/or B are alkenylene groups, can also be converted to a compound having an alkylene group except for the compound of the general formula (Id) by catalytic hydrogenating in the presence of a catalyst such as palladium-charcol, platinum dioxide, etc., under hydrogen gas-atmosphere.

In imidazole derivatives of this invention, one object compound of the invention can be converted to another object product by usual methods. For example, the compound of the general formula (Ic) can be prepared by hydrogenating the compound of the general formula (Ia) wherein $Y_1$ is a cyano group. The compound of the general formula (Ie) can also be prepared by hydrolyzing the compound of the general formula (Ia) wherein Y is a cyano group, according to usual methods, and if desired, N-di or mono-alkylating the obtained compound with an alkylation agent. Furthermore, the compound of the general formula (Ie) can also be converted to the compound of the general formula (Ia) wherein $Y_1$ is a carboxyl group by hydrolysis.

The compounds of the general formula (I) of this invention having a free carboxyl group or a free amino group can be converted according to usual methods to pharmaceutically acceptable salts thereof. For example, the free-form compound of the general formula (I) is dissolved in solvent, e.g., an alcohol, water, etc., an adequate amount of hydrochloric acid or sodium hydroxide is added to the solution, the mixture is stirred at room temperature for an adequate period of time, the solvent is then distilled away, and the residue is recrystallized to obtain the salt of the compound of the general formula (I). As examples of such pharmaceutically acceptable acid addition salts in addition to the hydrochloric acid salt, there are the sulfuric acid salt, the nitric acid salt, the phosphoric acid salt, the sulfonic acid salt, the benzoic acid salt, the succinic acid salt, the tartaric acid salt, the citric acid salt, etc. On the other hand, as examples of such pharmaceutically acceptable base additional salts, in addition to the sodium salt, there are the potassium salt, the calcium salt, the magnesium salt, etc.

In the case of the salts of the compounds of the general formula (I), the salt form of the compounds can be converted by usual methods to the free form of the compound thereof. For example, the salt form of the compound of the general formula (I) is dissolved in water, then an adequate amount of hydrochloric acid or sodium hydroxide is added to the solution, and the mixture is stirred at room temperature for an adequate period of time, water is removed, and the residue is distilled under reduced pressure or recrystallized from a solvent to obtain the desired compound.

Acid or base addition salts of the compounds of this invention have as high an inhibitory effect on thromboxane synthetase as the corresponding compounds having a free amino group or an acid group.

The imidazole derivatives of this invention possess a strong inhibitory effect on thromboxane synthetase, for example, P-(1-imidazolylmethyl)-α-methylcinnamic acid hydrochloric acid salt produce a 50% inhibition of thromboxane synthetase from rabbit platelet microsomes at the molar concentrations of $4 \times 10^{-9}$, and are useful as therapeutically active agents for the treatment of inflammation, hypertension, thrombus, cerebral apoplexy and asthma.

The imidazole derivatives of the general formula (I) and the pharmaceutically acceptable salts thereof of this invention can be administered to mammals including humans by oral, intravenous, intramuscular or intrarectal administration, and for administration they can be formulated into pharmaceutically compositions together with conventional pharmaceutical acceptable carriers.

The compounds can be administered in various forms according to the purposed therapy. Typical dosage forms which can be used are tablets, pills, powders, liquid preparations, suspensions, emulsions, granules, capsules, suppositories and injectable preparations.

In molding the pharmaceutical composition into a tablet form, a wide variety of conventional carriers known in this act can be used. Examples of suitable carriers are excipients, such as glucose, lactose, starch, cacao butter, hardened vegetable oils, kaolin and talc, binders, such as gum arabic powder, tragacanth powder, and ethanol, and disintegrants, such as laminaria and agar. The tablets, if desired, can be coated and made into sugar-coated tablets, gelatin-coated tablets, enteric-coated tablets, film-coated tablets, or tablets coated with two or more layers.

When the pharmaceutical composition is formulated into an injectable preparation, the resulting solution and suspension are preferably sterilized, and are isotonic with respect to blood. In making the pharmaceutical composition into a solution or suspension, all diluents customarily used in the art employed. Examples of suitable diluents are water, ethyl alcohol, propylene glycol, ethoxylate isostearyl alcohol, polyoxyethylene sorbitol, and sorbitan esters. Sodium chloride, glucose or glycerol may be incorporated into a therapeutic agent in an amount sufficient to prepare an isotonic solution. The therapeutic agent may further contain ordinary dissolving aids, buffers, pain-alleviating agents, and preservatives, and optionally, coloring agents, perfumes, flavors, sweeteners, and other drugs.

The dosage of the compound of this invention is about 1 mg to 1,000 mg/body by oral administration, or about 0.1 mg to 100 mg/body by parenteral administration per day in multiple doses depending upon the disease which is being treated.

This invention is further illustrated in more detail by way of the following examples wherein the melting point or the boiling point of the product obtained is uncorrected. Unless otherwise indicated, all parts, percents, ratios and the like are by weight.

EXAMPLE 1

Method A: Ethyl p-(1-imidazolylmethyl)cinnamate

To a suspension of 0.96 g of 50% sodium hydride in 50 ml of dry N,N-dimethylformamide was added 1.36 g of imidazole at room temperature, and then the mixture was stirred for 20 minutes.

A solution of 5.38 g of ethyl p-bromomethylcinnamate in 20 ml of dry N,N-dimethylformamide was added to the mixture at room temperature over a period of 20 minutes, and then the reaction mixture was stirred at the same temperature for 1 hour.

After concentration under vacuum at 40°–50° C., 100 ml of dichloromethane was added to the residual oil and washed with water and dried over anhydrous magnesium sulfate.

The solvent was evaporated and the residual oil was chromatographed on silica gel using chloroform, and the resulted crystals were recrystallized from ether to give 4.0 g of ethyl p-(1-imidazolylmethyl)cinnamate as colorless prisms; M.P. 89°–90° C.

IR-absorption spectrum (KBr): $\nu$CO: 1700 cm$^{-1}$. $\nu$C=C: 1640 cm$^{-1}$.

NMR spectrum (CDCl$_3$): $\delta$1.20 (t, 3H), 4.22 (q, 2H), 5.09 (s, 2H), 6.36 (d, 1H), 6.84 (br-s, 1H), 7.04 (br-s, 1H), 7.08 (d, 2H), 7.40 (d, 2H), 7.48 (br-s 1H), and 7.57 (d, 1H).

Elemental analysis as C$_{15}$H$_{16}$N$_2$O$_2$:

|  | C (%) | H (%) | N (%) |
|---|---|---|---|
| Calcd. | 70.29 | 6.29 | 10.93 |
| Found | 70.02 | 6.38 | 10.92 |

The following compounds were prepared in the same manner as described above. The results obtained are shown in Table 1 below.

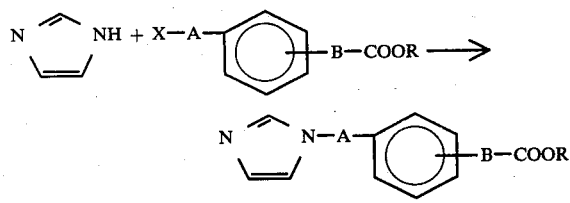

NMR spectrum (CDCl$_3$): $\delta$1.31 (t, 3H), 4.24 (q, 2H), 5.11 (s, 2H), 6.46 (d, 1H), 6.86 (br-s, 1H), 7.0-7.5 (m, 6H), and 7.57 (d, 2H).

Elemental analysis as C$_{15}$H$_{16}$O$_2$N$_2$:

|  | C (%) | H (%) | N (%) |
|---|---|---|---|
| Calcd. | 70.29 | 6.29 | 10.93 |
| Found | 70.09 | 6.32 | 10.67 |

Method C: Ethyl p-[$\beta$-(1-imidazolyl)ethyl]benzoate

A solution of 4.0 g of imidazole, 11.5 g of p-ethoxycarbonylphenetylbromide, and 7.5 g of di-isopropylethylamine in 200 ml of dry xylene was refluxed for 2.5 hours.

After cooling, the reaction mixture was washed with water, dried over anhydrous magnesium sulfate, and evaporated under reduced pressure.

The residual oil was chromatographed on silica gel using benzene-ethanol (20:1) to give 3.5 g of ethyl p-[$\beta$(1-imidazolyl)ethyl]benzoate as a pale brown oil.

IR-absorption spectrum (neat): $\nu$CO: 1705 cm$^{-1}$.

NMR spectrum (CDCl$_3$): $\delta$1.36 (t, 3H), 3.09 (t, 2H), 4.19 (t, 2H), 4.36 (q, 2H), 6.81 (t, 1H), 7.00 (br-s, 1H), 7.11 (d, 2H), 7.28 (br-s, 1H), and 7.95 (d, 2H).

Elemental analysis as C$_{14}$H$_{16}$O$_2$N$_2$:

Table 1

| X | A | B | R | Position | M.P.(°C.) | Yield (%) | IR(cm$^{-1}$) | NMR (CDCl$_3$) $\delta$ |
|---|---|---|---|---|---|---|---|---|
| Br | CH$_2$ | CH=CH | Et | o | 77.5–78 (colorless needles) | 45 | $\nu$CO: 1700 $\nu$C=C: 1635 (KBr) | 1.32(t,3H), 4.26(g,2H), 5.23 (s,2H), 6.31(d,1H), 6.84(m,1H), 7.03(m, 1H), and 7.87(d,2H). |
| Cl | CH$_2$ | CH=C\|Me | Et | p | oil | 60 |  |  |
| Br | CH$_2$ | CH=C\|Me | Et | p | oil | 55 | $\nu$CO: 1700 $\nu$C=C: 1630 (neat) | 1.33(t,3H),2.67(d,3H), 4.28(g, 2H), 5.13(s,2H), 6.87(br-s,1H), 7.06(br-s,1H), 7.12(d,2H), 7.33(d,2H), 7.51(br-s, 1H), and 7.61(br-s, 1H). |
| Ts | CH$_2$ | CH=C\|Me | Et | p | oil | 60 |  |  |
| Br | CH$_2$CH$_2$ | CH$_2$ | Me | p | oil | 25 | $\nu$CO: 1730 (neat) | 3.04(t,2H), 3.60(s,2H), 3.68(s, 3H), 4.16(t,2H), and 6.7–7.4 (m, 7H). |
| Br | CH$_2$CH=CH | — | Et | p | oil | 58 | $\nu$CO: 1710 (neat) | 1.41(t,3H), 4.41(q,2H), 4.77(d, 2H), 6.2–6.7(m,2H), 6.96(t,1H), 7.11(br-s,1H), 7.41(d,2H), 7.56(br-s,1H), and 8.01(d,2H). |

|  | C (%) | H (%) | N (%) |
|---|---|---|---|
| Calcd. | 68.83 | 6.60 | 11.47 |
| Found | 68.67 | 6.48 | 11.41 |

Method B: Ethyl m-(1-imidazolylmethyl)cinnamate

A solution of 2.72 g (2 equivalents) of imidazole and 5.4 g (1 equivalent) of ethyl m-bromomethylcinnamate in 15 ml of N,N-dimethylformamide was heated at 150° C. for 6 hours.

After concentration under vacuum, the residual oil was dissolved in dichloromethane and washed with water, dried over anhydrous magnesium sulfate, and evaporated under reduced pressure. The residual brown oil was chromatographed on silica gel using dichloromethane to give 2.5 g of ethyl m-(1-imidazolylmethyl)cinnamate as a brown oil.

IR-absorption spectrum (neat): $\nu$CO: 1710 cm$^{-1}$. $\nu$C=C: 1640 cm$^{-1}$.

Method D: Ethyl p-(1-imidazolylmethyl)cinnamate

A solution of 0.68 g of imidazole, 2.7 g of ethyl p-bromomethylcinnamate and 0.1 g of tetra-n-butylammonium bromide (phase transfer catalyst) in 30 ml of benzene and 30 ml of 50% aqueous sodium hydroxide was vigorously stirred at room temperature for 6 hours. The organic phase was then separated and washed with water and dried over anhydrous magnesium sulfate.

The solvent was evaporated and the residue was chromatographed on silica gel using chloroform, and the resulted solid was recrystallized from ether to give 1.5 g of ethyl p-(1-imidazolylmethyl)cinnamate as the same product by the Method A.

Method E: Ethyl p-(1-imidazolylmethyl)-α-methylcinnamate

A mixture of 2.04 g of imidazole, 7.2 g of ethyl p-chloromethyl-α-methylcinnamate, 4.5 g of anhydrous potassium carbonate, and 0.1 g of 18-crown-6 in 50 ml of acetonitrile was stirred at room temperature for 15 hours.

After filtration, the filtrate was evaporated under reduced pressure, and the residual oil was dissolved in dichloromethane, washed with water, dried over anhydrous magnesium sulfate, and evaporated under reduced pressure.

The residual oil was chromatographed on silica gel using dichloromethane-ethanol (20:1) to give 4.3 g of ethyl p-(1-imidazolylmethyl)-α-methylcinnamate as a colorless oil.

IR-absorption spectrum (neat): $\nu$CO: 1700 cm$^{-1}$.

NMR spectrum (CDCl$_3$): δ1.33 (t, 3H), 2.07 (d, 3H), 4.28 (q, 2H), 5.13 (s, 2H), 6.87 (br-s, 1H), 7.06 (br-s, 1H), 7.12 (d, 2H), 7.33 (d, 2H), 7.51 (br-s, 1H), and 7.61 (br-s, 1H).

Elemental analysis as $C_{16}H_{18}O_2N_2$:

|  | C (%) | H (%) | N (%) |
|---|---|---|---|
| Calcd. | 71.09 | 6.71 | 10.36 |
| Found | 70.95 | 6.58 | 10.14 |

Method F: Ethyl p-(1-imidazolylmethyl)cinnamate

A suspension of 1.75 g of silver salt of imidazole, which was prepared from imidazole and silver nitrate in a sodium hydroxide solution, and 2.7 g of ethyl p-bromomethylcinnamate in 50 ml of N,N-dimethylformamide was heated at 100° C. for 7 hours.

After removal of the solvent, 30 ml of dichloromethane and 30 ml of water was added to the residue and the organic phase was separated.

The dichloromethane solution was dried over anhydrous magnesium sulfate and evaporated under reduced pressure.

The residual oil was chromatographed on silica gel using chloroform to give 1.2 g of ethyl p-(1-imidazolylmethyl) cinnamate as the same product by the Method A.

Method G: Ethyl p-(1-imidazolyl)cinnamate

A mixture of 3.4 g of imidazole, 12.0 g of ethyl p-bromocinnamate, 6.5 g of anhydrous potassium carbonate, and 0.3 g of cupric bromide in 20 ml of nitrobenzene was heated at 170°–180° C. for 30 hours.

After cooling, the reaction mixture was diluted with 200 ml of dichloromethane and filtered. The filtrate was concentrated under reduced pressure and the residual dark brown oil (containing nitrobenzene) was chromatographed on silica gel using benzene (to remove the nitrobenzen), followed by chloroform, and the resulted solid was recrystallized from ether to give 5.0 g of ethyl p-(1-imidazolyl)cinnamate as pale brown leaflets; M.P. 96°–97.5° C.

IR-absorption spectrum (KBr): $\nu$CO: 1700 cm$^{-1}$. $\nu$C=C: 1640 cm$^{-1}$.

NMR spectrum (CDCl$_3$): δ1.33 (t, 3H), 4.30 (q, 2H), 6.44 (d, 1H), 7.21 (br-s, 1H), 7.31 (br-s, 1H), 7.41 (d, 2H), 7.63 (d,2H), 7.69 (d, 1H), and 7.90 (br-s, 1H).

Elemental analysis as $C_{14}H_{14}O_2N_2$:

|  | C (%) | H (%) | N (%) |
|---|---|---|---|
| Calcd. | 69.40 | 5.83 | 11.56 |
| Found | 69.48 | 5.96 | 11.52 |

The following compounds were prepared in the same manner as described above. The results obtained are shown in Table 2 below.

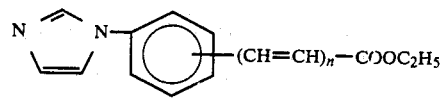

Table 2

| n | Position | M.P.(°C.) | Yield (%) | IR (cm$^{-1}$) | NMR (CDCl$_3$) δ |
|---|---|---|---|---|---|
| 2 | m | oil | 25 | $\nu$CO: 1700<br>$\nu$C=C: 1630<br>(neat) | 1.32(t,3H), 4.25(q,2H), 6.04(d,1H), 6.85–6.95(m,2H), 7.15–7.55(m,7H), and 7.86(br-s,1H). |
| 2 | p | 126–127<br>(colorless<br>needles) | 30 | $\nu$CO: 1695<br>$\nu$C=C: 1620<br>(KBr) | 1.30(t,3H), 4.23(q,2H), 6.01(d,1H), 6.8–6.95(m,2H), 7.1–7.6(m,7H), and 7.84(br-s,1H). |

Method H: Ethyl 5-[p-(1-imidazolyl)phenyl]-2,4-pentadienoate

A mixture of 3.4 g of imidazole, 9.3 g of p-bromobenzaldehyde, 6.9 g of anhydrous potassium carbonate, and 0.3 g of cuprous bromide in 20 ml of nitrobenzene was heated at 160° C. for 18 hours under stirring.

After cooling, by the same procedure as described in Method G of Example 1, 3.5 g of p-(1-imidazolyl)benzaldehyde was given as pale yellow crystals.

To a stirred suspension of 0.7 g of 50% sodium hydride in 40 ml of dry tetrahydrofuran was added 3.63 g of diethyl 3-ethoxycarbonyl-2-propenylphosphonate in 20 ml of dry tetrahydrofuran at room temperature over a period of 20 minutes under a nitrogen atmosphere. A solution of 2.5 g of p-(1-imidazolyl) benzaldehyde in 50 ml of dry tetrahydrofuran was added to the mixture at room temperature over a period of 20 minutes, and the mixture was stirred for 2 hours.

The mixture was then treated with a saturated aqueous solution of ammonium chloride and filtered. The filtrate was concentrated under reduced pressure and the residue was dissolved in 80 ml of dichloromethane. The solution was washed with a saturated aqueous solution of sodium bicarbonate and water, and dried over anhydrous magnesium sulfate.

After evaporation under reduced pressure, the residue was chromatographed on silica gel using benzene-chloroform (1:2) and the resulted solid was recrystallized from dichloromethane-ether to give 0.75 g of ethyl 5-[p-(1-imidazolyl) phenyl]-2,4-pentadienoate as colorless needles; M.P. 126°–127° C.

IR-absorption spectrum (KBr): $\nu$CO: 1695 cm$^{-1}$. $\nu$C=C: 1620 cm$^{-1}$.

NMR spectrum CDCl$_3$): δ1.30 (t, 3H), 4.23 (q, 2H), 6.01 (d, 1H), 6.8–6.95 (m, 2H), 7.1–7.6 (m, 7H), and 7.84 (br-s, 1H).

Elemental analysis as C$_{16}$H$_{16}$O$_2$N$_2$:

|  | C (%) | H (%) | N (%) |
| --- | --- | --- | --- |
| Calcd. | 71.61 | 6.01 | 10.44 |
| Found | 71.88 | 5.94 | 10.15 |

Method I: Ethyl 3-[p-(1-imidazolylmethyl)phenyl]propionate

A solution of 10 g of ethyl p-(1-imidazolylmethyl) cinnamate, which was prepared by the Method A in Example 1, in 120 ml of ethanol was hydrogenated over 0.6 g of 10% palladium-on-carbon at room temperature under atmospheric pressure.

After filtration and evaporation under reduced pressure, the residual solid was recrystallized from petroleum ether to give 8.5 g of ethyl 3-[p-(1-imidazolylmethyl)phenyl]propionate as colorless prisms; M.P. 34°–35° C.

IR-absorption spectrum (KBr): νCO: 1730 cm$^{-1}$.

NMR spectrum (CDCl$_3$): δ1.18 (t, 3H), 2.45–2.75 (m, 2H), 2.80–3.10 (m, 2H), 4.10 (q, 2H), 5.03 (s, 2H), 6.82 (t, 1H), 7.00 (br-s, 1H), 7.01 (d, 2H), 7.13 (d, 2H), and 7.46 (br-s, 1H).

Elemental analysis as C$_{15}$H$_{18}$O$_2$N$_2$:

|  | C (%) | H (%) | N (%) |
| --- | --- | --- | --- |
| Calcd. | 69.74 | 7.02 | 10.85 |
| Found | 69.89 | 7.23 | 10.65 |

The following compounds were prepared in the same manner as described above. The results obtained are shown in Table 3 below.

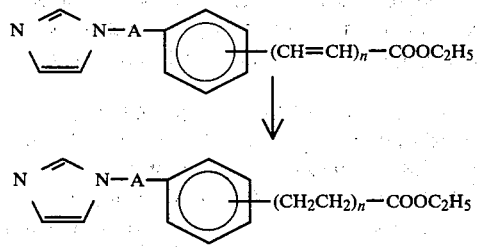

Table 3

| A | n | Position | M.P.(°C.) | Yield (%) | IR (cm$^{-1}$ Neat) | NMR (CDCl$_3$) δ |
| --- | --- | --- | --- | --- | --- | --- |
| CH$_2$ | 1 | m | oil | 70 | νCO: 1730 | 1.19(t,3H), 2.45–2.70(m, 2H), 2.75–3.05(m,2H), 4.09(q,2H), 5.04(s,2H), 6.75–7.35(m,6H), and 7.47(br-s,1H). |
| — | 2 | m | oil | 70 | νCO: 1725 | 1.22(t,3H), 1.55–1.80(m,4H), 2.2–2.45(m,2H), 2.6–2.8(m,2H), 4.12(q,2H), 7.05–7.35(m,6H), and 7.81(br-s,1H). |

EXAMPLE 2

3-[p-(1-Imidazolylmethyl)phenyl]propanol

To a suspension of 0.62 g of lithium aluminum hydride in 30 ml of dry tetrahydrofuran was added 4.0 g of ethyl 3-[p-(1-imidazolylmethyl)phenyl]propionate, which was prepared by the Method I in Example 1, in 30 ml of dry tetrahydrofuran over a period of 10 minutes at room temperature, and then the reaction mixture was refluxed for 2 hours.

After cooling, the mixture was treated with 10% sodium hydroxide and filtered. The filtrate was dried over anhydrous magnesium sulfate and evaporated under reduced pressure.

The residual oil was chromatographed on silica gel using chloroform to give 3.0 g of 3-[p-(1-imidazolylmethyl)phenyl]propanol as colorless crystals; M.P. 44°–45° C. IR-absorption spectrum (KBr): νOH: 3230 cm$^{-1}$.

NMR spectrum (CDCl$_3$):

δ1.65–2.00 (m, 2H), 2.70 (t, 2H), 3.62 (t, 2H), 3.82 (br-s, 1H), 5.01 (s, 2H), 6.72 (t, 1H), 6.9–7.2 (m, 5H), and 7.44 (br-s, 1H).

Elemental analysis as C$_{13}$H$_{16}$ON$_2$:

|  | C (%) | H (%) | N (%) |
| --- | --- | --- | --- |
| Calcd. | 72.19 | 7.46 | 12.95 |
| Found | 72.38 | 7.21 | 12.69 |

EXAMPLE 3

3-[m-(1-Imidazolylmethyl)phenyl]propanol

By the same procedure as described in Example 2, 3-[m-(1-imidazolylmethyl)phenyl]propanol was prepared from ethyl 3-[m-(1-imidazolylmethyl)phenyl]propionate, which was prepared by the Method H in Example 1, in 97% yield as a colorless oil.

IR-absorption spectrum (neat): νOH: 3250 cm$^{-1}$.

NMR spectrum (CDCl$_3$): δ1.65–2.10 (m, 2H), 2.70 (t, 2H), 3.64 (t, 2H), 5.03 (s, 2H), 6.80–7.35 (m, 6H), and 7.46 (br-s, 1H).

Elemental analysis as C$_{13}$H$_{16}$ON$_2$:

|  | C (%) | H (%) | N (%) |
| --- | --- | --- | --- |
| Calcd. | 72.19 | 7.46 | 12.95 |
| Found | 72.42 | 7.58 | 12.70 |

EXAMPLE 4

Method A:

β-[p-(1-Imidazolylmethyl)phenyl]acrylonitrile

To a suspension of 0.48 g of 50% sodium hydride in 30 ml of dry N,N-dimethylformamide was added 0.68 g of imidazole at room temperature, and then the mixture was stirred for 15 minutes.

A solution of 2.22 g of β-(p-bromomethylphenyl)acrylonitrile in 20 ml of dry N,N-dimethylformamide was added to the mixture over a period of 20 minutes at room temperature, and then the reaction mixture was stirred at the same temperature for 15 hours.

After concentration under vacuum, the residue was dissolved in 50 ml of dichloromethane and washed with water, dried over anhydrous magnesium sulfate, and evaporated under reduced pressure. The residue was chromatographed on silica gel using dichloromethane-ethanol (20:1) and the resulted solid was recrystallized from ethanol-ether-petroleum ether to give 1.1 g of β-[p-(1-imidazolylmethyl)phenyl]acrylonitrile as pale yellow needles; M.P. 118°–119.5° C.

IR-absorption spectrum (KBr): νCN: 2210 cm$^{-1}$. νC=C: 7615 cm$^{-1}$.

NMR spectrum (CDCl$_3$): δ5.14 (s, 2H), 5.85 (d, 1H), 6.88 (m, 1H), 7.08 (m, 1H), 7.18 (d, 2H), 7.34 (d, 1H), 7.40 (d, 2H), and 7.53 (br-s, 1H).

Elemental analysis as C$_{13}$H$_{11}$N$_3$:

|  | C (%) | H (%) | N (%) |
|---|---|---|---|
| Calcd. | 74.62 | 5.30 | 20.08 |
| Found | 74.73 | 5.36 | 20.08 |

Method B: p-[γ-(1-Imidazolyl)propyl]benzonitrile

To a suspension of 0.96 g of 50% sodium hydride in 30 ml of dry N,N-dimethylformamide was added slowly 1.54 g of imidazole at room temperature, and then the mixture was heated to 80° C.

A solution of 4.8 g of 3-(p-bromophenyl)propylchloride in 30 ml of dry N,N-dimethylformamide was added to the mixture at 80° C. over a period of 30 minutes, and then the reaction mixture was heated for 30 minutes at the same temperature.

After concentration under vacuum, the residual oil was dissolved in 80 ml of dichloromethane, washed with water, dried over anhydrous magnesium sulfate, and evaporated under reduced pressure.

The residual oil was chromatographed on silica gel using chloroform-ethanol (20:1) to give 4.0 g of p-[γ-(1-imidazolyl)propyl]phenylbromide as a colorless oil.

NMR spectrum (CDCl$_3$): δ1.9–2.3 (m, 2H), 2.57 (t, 2H), 3.91 (t, 2H), 6.85 (br-s, 1H), 6.96 (d, 2H), 7.00 (t, 1H), 7.35 (d, 2H), and 7.39 (br-s, 1H).

Then a solution of 4.0 g of p-[γ-(1-imidazolyl)propyl]phenylbromide and 2.2 g of cuprous cyanide in 15 ml of dry N,N-dimethylformamide was refluxed for 6 hours.

The hot reaction mixture was poured into a warm solution of 3 g of sodium cyanide in 15 ml of water. After shaking the mixture vigorously, the mixture was extracted with benzene.

The benzene extract was washed with 20 ml of 10% aqueous sodium cyanide solution and water, and then dried over anhydrous magnesium sulfate.

After removal of solvent, the residual oil was chromatographed on silica gel using chloroform to give 2.0 g of p-[γ-(1-imidazolyl)propyl]benzonitrile as a pale brown oil.

IR-absorption spectrum (neat): νCN: 2230 cm$^{-1}$.

NMR spectrum (CDCl$_3$): δ2.0–2.4 (m, 2H), 2.69 (t, 2H), 3.97 (t, 2H), 6.87 (t, 1H), 7.03 (br-s, 1H), 7.21 (d, 2H), 7.41 (br-s, 1H), and 7.53 (d, 2H).

Elemental analysis as C$_{13}$H$_{13}$N$_3$:

|  | C (%) | H (%) | N (%) |
|---|---|---|---|
| Calcd. | 73.90 | 6.20 | 19.89 |
| Found | 73.67 | 6.31 | 19.61 |

Method C: 3-[p-(1-Imidazolyl)phenyl]propionitrile

A mixture of 2.8 g of imidazole, 7.6 g of 3-(p-bromophenyl)propionitrile, 4.7 g of anhydrous potassium carbonate, and 0.4 g of cuprous bromide in 15 ml of nitrobenzene was heated at 160° C. for 25 hours under stirring.

After cooling, the mixture was diluted with 200 ml of dichloromethane and filtered. The filtrate was evaporated under reduced pressure and the residual oil (containing nitrobenzene) was chromatographed on silica gel using benzene (to remove the nitrogenzene), followed by dichloromethane to give 5.7 g of 2-[p-(1-imidazolyl)phenyl]propionitrile as a pale brown oil.

IR-absorption spectrum (neat): νCN: 2240 cm$^{-1}$.

NMR spectrum (CDCl$_3$):
δ1.85–2.20 (m, 2H), 22.40 (t, 2H), 2.87 (t, 2H), 7.20 (br-s, 1H), 7.26 (m, 1H), 7.30 (s, 4H), and 7.84 (br-s, 1H).

Elemental analysis as C$_{13}$H$_{13}$N$_3$:

|  | C (%) | H (%) | N (%) |
|---|---|---|---|
| Calcd. | 73.90 | 6.20 | 19.89 |
| Found | 73.62 | 6.31 | 19.59 |

Method D:
4-[p-(1-Imidazolylmethyl)phenyl]butyronitrile

To a solution of 2.4 g of 3-[p-(1-imidazolylmethyl)phenyl]propanol, which was prepared in Example 2, in 30 ml of dry benzene was added 5 ml of thionyl chloride at room temperature, and then the solution was refluxed for 1.5 hours.

After evaporation under reduced pressure, the residual oil was neutralized with saturated sodium carbonate and extracted with dichloromethane. The solution was dried over anhydrous magnesium sulfate and evaporated under reduced pressure to give 2.0 g of 3-[p-(1-imidazolylmethyl)phenyl]propylchloride as a brown oil.

Then a solution of 2.0 g of the chloride in 7 ml of dimethyl sulfoxide was added to a stirred solution of 0.52 g of sodium cyanide in 10 ml of dimethyl sulfoxide at 40° C. over a period of 10 minutes, and the reaction mixture was heated at 100° C. for 5 hours. The reaction mixture was poured into 100 ml of water and the aqueous mixture was extracted with dichloromethane, and dried over anhydrous magnesium sulfate.

The extract was evaporated and the residual oil was chromatographed on silica gel using chloroform to give 1.5 g of 4-[p-(1-imidazolylmethyl)phenyl]butyronitrile as a pale brown oil.

IR-absorption spectrum (neat): νCN: 2245 cm$^{-1}$.

NMR spectrum (CDCl$_3$): δ1.80–2.10 (m, 2H), 2.30 (t, 2H), 2.76 (t, 2H), 5.05 (s, 2H), 6.84 (t, 1H), 7.08 (s, 4H), 7.10 (br-s, 1H), and 7.48 (br-s, 1H).

Elemental analysis as C$_{14}$H$_{15}$N$_3$:

|  | C (%) | H (%) | N (%) |
|---|---|---|---|
| Calcd. | 74.64 | 6.71 | 18.65 |
| Found | 74.92 | 6.83 | 18.36 |

EXAMPLE 5

4-[m-(1-Imidazolylmethyl)phenyl]butyronitrile

By the same procedure as described by the Method D in Example 4, 4-[m-(1-imidazolylmethyl)phenyl]butyronitrile was prepared from 3-[m-(1-imidazolylmethyl)phenyl]propanol, which was prepared in Example 3, in 42% yield as a pale brown oil.

IR-absorption spectrum (neat): $\nu$CN: 2240 cm$^{-1}$.

NMR spectrum (CDCl$_3$):

$\delta$1.75–2.15 (m, 2H), 2.02–2.45 (m, 2H), 2.76 (t, 2H), 5.07 (s, 2H), 5.80–7.35 (m, 6H), and 7.48 (br-s, 1H).

Elemental analysis as C$_{14}$H$_{15}$N$_3$:

|  | C (%) | H (%) | N (%) |
|---|---|---|---|
| Calcd. | 74.64 | 6.71 | 18.65 |
| Found | 74.87 | 6.92 | 18.37 |

EXAMPLE 6

Method A: p-(1-Imidazolylmethyl)cinnamic acid hydrochloride

A solution of 2.0 g of ethyl p-(1-imidazolylmethyl)cinnamate, which was prepared by the Method A in Example 1, and 1.0 g of sodium hydroxide in 30 ml of methanol-water (1:2) was stirred for 2 hours at room temperature.

After concentration under reduced pressure, an excess of diluted hydrochloric acid was added to the residue and the acidic solution was concentrated under reduced pressure to remove the hydrochloric acid completely.

The residual solid was dissolved in ethanol and the insoluble salts were filtered off.

The filtrate was evaporated and the residual crystals were recrystallized from ethanol-ether to give 1.4 g of p-(1-imidazolylmethyl)cinnamic acid hydrochloride as colorless crystals; M.P. 214°–217° C.

IR-absorption spectrum (KBr): $\nu$CO: 1690 cm$^{-1}$.

NMR spectrum (DMSO-D$_6$): $\delta$5.50 (s, 1H), 6.51 (d, 1H), 7.25–7.85 (m, 7H), and 9.43 (br-s, 1H).

Elemental analysis as C$_{13}$H$_{12}$O$_2$N$_2$.HCl:

|  | C (%) | H (%) | N (%) |
|---|---|---|---|
| Calcd. | 59.98 | 4.95 | 10.58 |
| Found | 58.81 | 4.90 | 10.60 |

The following compounds were prepared in the same manner as described above. The results obtained are shown in Table 4 below.

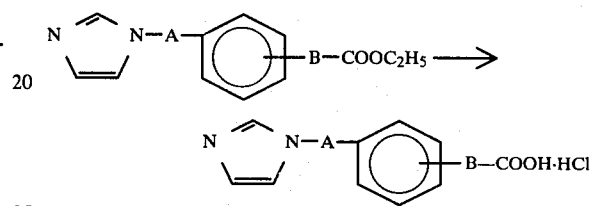

Table 4

| A | B | Position | M.P. (°C.) Yield (%) | IR(cm$^{-1}$:KBr) | NMR (DMSO-D$_6$) $\delta$ |
|---|---|---|---|---|---|
| CH$_2$ | CH=CH | o | 201–203.5  60 colorless prisms | $\nu$CO: 1700 $\nu$C=C: 1625 | 5.74(s,2H),6,47(d,1H), 7.10–7.80(m,6H), 7.87(d,1H), and 9.23(br-s, 1H). |
| CH$_2$ | CH=CH | m | 119–120  50 colorless leaflets | $\nu$CO: 1695 $\nu$C=C: 1630 | 5.51(s,2H), 6.56(d,1H), 7.35–8.0(m,7H), 9.46(br-s,1H), and 10.8–12.7(br.2H). |
| CH$_2$ | CH$_2$CH$_2$ | p | 165–167  81 colorless needles | $\nu$CO: 1745 | 2.4–2.65(m,2H), 2.65–2.95(m,2H), 5.42(s,2H), 7.21(d,2H), 7.32(d,2H), 7.63(t,1H), 7.78 (t,1H), 9.40(br-s,1H), and 11.5–13.3(br.2H). |
| CH$_2$ | CH$_2$CH$_2$ | m | 115–116  50 colorless needles | $\nu$CO: 1710 | 2.45–2.75(m,2H), 2.75–3.05(m,2H), 5.45(s,2H), 7.20–7.45(m,4H), 7.68(t,1H), 7.82(t,1H), and 9.35(br-s,1H). |
| — | CH=CH | p | >300  58 colorless needles | $\nu$CO: 1695 $\nu$C=C: 1635 | 6.68(d,1H), 7.69(d,1H), 7.84(m,1H), 7.92 (s,4H), 8.32(m,1H), and 9.69(br-s,1H). |
| — | (CH$_2$)$_4$ | m | 155–156  50 pale brown leaflets | $\nu$CO: 1710 | 1.4–1.8(m,4H), 2.28(t,2H), 2.6–2.85(m,2H), 7.3–7.95(m,5H), 8.30(t,1H), and 9.78(br-s, 1H). |
| — | (CH=CH)$_2$ | p | 260(dec.)  50 pale yellow crystals | $\nu$CO: 1670 $\nu$C=C: 1620 | 5.95–6.2(m,1H), 7.1–7.4(m,3H), 7.7–8.0 (m,5H), 8.32(br-s,1H), and 9.80(br-s,1H). |
| CH$_2$CH=CH | — | p | 284–287  50 colorless crystals | $\nu$CO: 1690 | 5.09(d,2H), 6.60–6.80(m,2H), 7.55(d,2H), 7.70(br-s,1H), 7.82(m,1H), 7.88(d2H) and 9.30(br-s,1H). |
| CH$_2$CH$_2$ | — | p | 214–215.5  50 pale yellow prisms | $\nu$CO: 1665 | 3.30(t,2H), 4.58(t,2H), 7.37(d,2H), 7.67(m, 1H), 7.83(m,1H), 7.87(d,2H), and 9.17(m,1H). |
| CH$_2$CH$_2$ | CH$_2$ | p | 150–152  71 colorless prisms | $\nu$CO: 1715 | 3.16(t,2H), 3.55(s,2H), 4.49(t,2H), 7.13 (s,4H), 7.62(t,1H), 7.79(t,1H), and 9.17 (br-s,1H). |
| CH$_2$ | CH=C$\underset{\text{Me}}{\vert}$ | p | 209–213 colorless needles | $\nu$CO: 1675 | 2.00(d,3H), 5.55(s,1H), 7.44(s,4H), 7.53(d, 1H), 7.67(t,1H), 7.85(t,1H), and 9.49(br-s,1H). |
| — | (CH=CH)$_2$ | m | 205–208(dec.) 50 pale brown leaflets | $\nu$CO: 1690 $\nu$C=C: 1615 | 6.0–6.2(m,1H), 7.05–8.2(m,8H), 8.40(br-s,1H), and 9.89(br-s,1H). |

Method B: p-[$\gamma$-(1-Imidazolyl)propyl]benzoic acid hydrochloride

A solution of 1.0 g of p-[$\gamma$-(1-imidazolyl)propyl]benzonitrile, which was prepared by the Method B in Example 3, in 10 ml of concentrated hydrochloric acid was refluxed for 3 hours.

After removal of the hydrochloric acid under reduced pressure, the residual solid was dissolved in ethanol and the insoluble salts were filtered off.

The filtrate was evaporated under reduced pressure and the residual crystals were recrystallized from ethanol to give 0.7 g of p-[$\gamma$-(1-imidazolyl)propyl]benzoic acid hydrochloride as colorless leaflets; M.P. 200°–203° C.

IR-absorption spectrum (KBr): νCO: 1700 cm⁻¹.

NMR spectrum (DMSO-D₆): δ2.0–2.4 (m, 2H), 2.45–2.85 (m, 2H), 4.29 (t, 2H), 7.31 (d, 2H), 7.66 (t, 1H), 7.83 (d, 2H), 7.84 (t, 1H), and 9.28 (br-s, 1H).

Elemental analysis as C₁₃H₁₄O₂N₂·HCl:

|  | C(%) | H (%) | N (%) |
|---|---|---|---|
| Calcd. | 58.54 | 5.67 | 10.50 |
| Found | 58.63 | 5.73 | 10.55 |

The following compounds were prepared in the same manner as described above. The results obtained are shown in Table 5.

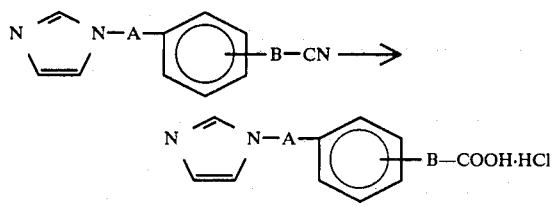

Method C: 3-[p-(1-Imidazolylmethyl)phenyl]propionic acid hydrochloride

To a suspension of 0.96 g of 50% sodium hydride in 50 ml of dry N,N-dimethylformamide was added 1.4 g of imidazole at room temperature, and then the mixture was stirred for 20 minutes.

A solution of 4.5 g of 4-(p-bromomethylphenyl)-1-butene in 20 ml of dry N,N-dimethylformamide was added to the mixture at 70° C. over a period of 30 minutes, and then the reaction mixture was stirred at the same temperature for 1 hour.

After concentration under vacuum, 100 ml of dichloromethane was added to the residual oil and washed with water and dried over anhydrous magnesium sulfate.

The solvent was evaporated under reduced pressure to give 2.3 g of 4-[p-(1-imidazolylmethyl)phenyl]-1-butene as a crude pale yellow oil.

IR-absorption spectrum (neat): νC=C: 1630 cm⁻¹.

NMR spectrum (DMSO-D₆): δ2.2–2.45 (m, 2H), 2.5–2.8 (m, 2H), 4.95–5.2 (m, 2H), 5.15 (s, 2H), 5.55–6.05 (m, 1H), 6.88 (br-s, 1H), 7.1–7.3 (m, 5H), and 7.72 (br-s, 1H).

To a solution of 4.3 g of potassium permanganate and 0.4 g of dicyclohexyl-18-crown-6 in 60 ml of benzene was added 2.3 g of 4-[p-(1-imidazolylmethyl)phenyl]-1-butene and the mixture was stirred at room temperature for 5 hours.

The resulting precipitates were separated from the solution by filtration and suspended in aqueous potassium hydroxide.

The insoluble solid was filtered off and the filtrate was washed with ether.

The aqueous layer was acidified with concentrated hydrochloric acid and then evaporated under reduced pressure to remove the hydrochloric acid completely.

The residual solid was dissolved in ethanol and the insoluble salts were filtered off.

The filtrate was evaporated and the residual crystals were recrystallized from ethanol-ether to give 1.4 g of 3-[p-(1-imidazolylmethyl)phenyl]propionic acid hydrochloride as the same product by the Method A in Example 6 (Table 4).

EXAMPLE 7

Ethyl 4-[p-(1-imidazolylmethyl)phenyl]butyrate

A solution of 0.8 g of 4-[p-(1-imidazolylmethyl)phenyl]butyric acid hydrochloride in 40 ml of absolute ethanol was saturated with dry hydrogen chloride gas on an ice-bath, and the solution was stirred for 1 hour at room temperature.

After concentration under reduced pressure, 20 ml of 10% aqueous sodium carbonate solution was added to the residue and the aqueous mixture was extracted with dichloromethane.

The extract was washed with water, dried over anhydrous magnesium sulfate, and evaporated under reduced pressure.

The residual oil was chromatographed on silica gel using dichloromethane to give 0.6 g of ethyl 4-[p-(1-imidazolylmethyl)phenyl]butyrate as a colorless oil.

IR-absorption spectrum (neat): νCO: 1725 cm⁻¹.

NMR spectrum (CDCl₃): δ1.23 (t, 3H), 1.80–2.10 (m, 2H), 2.20–2.40 (m, 2H), 2.64 (t, 3H), 4.10 (q, 2H), 5.04 (s, 2H), 6.83 (br-s, 1H), 7.00 (d, 2H), 7.02 (br-s, 1H), 7.10 (d, 2H), and 7.47 (br-s, 1H).

Elemental analysis as C₁₆H₂₀O₂N₂:

|  | C (%) | H (%) | N (%) |
|---|---|---|---|
| Calcd. | 70.56 | 7.40 | 10.29 |
| Found | 70.26 | 7.64 | 10.04 |

The following compounds were prepared in the same manner. The results obtained are shown in Table 6 below.

Table 5

| A | B | Position | M.P. (°C.) | Yield(%) | IR(cm⁻¹:KBr) | NMR (DMSO-D₆) δ |
|---|---|---|---|---|---|---|
| CH₂ | (CH₂)₃ | p | 186–188.5 | 95 | νCO: 1750 | 1.65–1.95(m,2H), 2.21(t,2H), 2.59(t,2H), 5.43(s,2H), 7.18(d,2H), 7.33(d,2H), 7.62 (t,1H), 7.78(t,1H), and 9.39 (br-s,1H). |
| CH₂ | (CH₂)₃ | m | 106–107 | 95 | νCO: 1720 | 1.65–2.00(m,2H), 2.26(t,2H), 2.63(t,2H), 5.48(s,2H), 7.2–7.4(m,4H), 7.69(t,1H), 7.83 (t,1H), and 9.42(m,1H). |
| — | (CH₂)₃ | p | 153–154 | 50 | νCO: 1715 | 1.75–2.10(m,2H), 2.28(t,2H) 2.72(t,2H), 7.43(d,2H), 7.75 (d,2H), 7.88(m,1H), 8.27(m,1H), and 9.78(br-s,1H). |

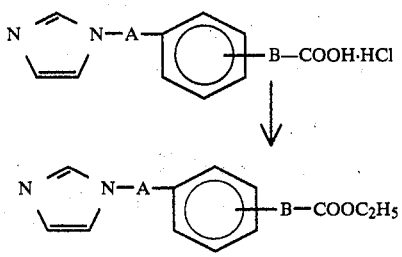

Table 6

| A | B | Position | M.P. (°C.) | Yield (%) | IR(cm$^{-1}$) | NMR (CDCl$_3$) δ |
|---|---|---|---|---|---|---|
| CH$_2$ | (CH$_2$)$_3$ | m | oil | 50 | νCO: 1725 | 1.23(t,3H), 1.70-2.10(m,2H), 2.20-2.45(m,2H), 2.63(t,2H), 4.12(q,2H), 5.50(s,2H), 6.8-7.3(m,6H), and 7.49(br-s, 1H). |
| — | (CH$_2$)$_3$ | p | oil | 60 | νCO: 1720 | 1.25(t,3H), 1.85-2.15(m,2H), 2.25-2.5(m,2H), 2.71(t,2H), 4.14(q,2H), 7.15(br-s,1H), 7.2-7.35(m,5H), and 7.78(br-s,1H). |
| (CH$_2$)$_3$ | — | p | oil | 75 | νCO: 1710 | 1.37(t,3H), 1.95-2.35(m,2H), 2.67 (t,2H), 3.95(t,2H), 4.37(q,2H 6.93(br.1H), 7.07(br.1H), 7.19(d, 2H), 7.45(br,1H), and 7.95(d,2H). |

EXAMPLE 8

3-[p-(1-Imidazolylmethyl)phenyl]propylamine dihydrochloride

Method A: A solution of 160 mg of β-[p-(1-amidazolylmethyl) phenyl]acrylonitrile, which was prepared by the Method A in Example 4, in 1 ml of concentrated hydrochloric acid and 50 ml of ethanol was hydrogenated over 20 mg of platinum dioxide at room temperature under 4 atms.

After filtration and concentration under reduced pressure, the residual crystals were recrystallized from ethanol-ether to give 120 mg of 3-[p-(1-imidazolylmethyl)phenyl]propylamine dihydrochloride as colorless prisms; M.P. 233°-235° C.

NMR spectrum (DMSO-D$_6$): δ1.75-2.1 (m, 2H), 2.5-3.0 (m, 4H), 5.47 (s, 2H), 7.23 (d, 2H), 7.39 (d, 2H), 7.68 (t, 1H), 7.84 (t, 1H), 8.2-8.6 (br. 2H), and 9.48 (br-s, 1H).

Elemental analysis as C$_{13}$H$_{17}$N$_3$.2HCl:

| | C (%) | H (%) | N (%) |
|---|---|---|---|
| Calcd. | 54.17 | 6.64 | 14.58 |
| Found | 54.07 | 6.80 | 14.53 |

Method B: To a solution of 2.4 g of 3-[p-(1-imidazolylmethyl)phenyl]propanol, which was prepared in Example 2, in 30 ml of dry benzene was added 5 ml of thionyl chloride at room temperature, and then the solution was refluxed for 1.5 hours.

After evaporation under reduced pressure, the residual oil was neutralized with saturated sodium carbonate and extracted with dichloromethane. The extract was dried over anhydrous magnesium sulfate and evaporated under reduced pressure to give 2.0 g of 3-[p-(1-imidazolylmethyl)phenyl]propylchloride as a brown oil.

Then a solution of 2.0 g of the chloride in 20 ml of ammonia-saturated ethanol was stirred in a sealed tube for 24 hours at room temperature.

After evarporation under reduced pressure, the residue was dissolved in 10 ml of concentrated hydrochloric acid and the solution was concentrated under vacuum.

The residual solid was recrystallized from ethanol-ether to give 1.0 g of 3-[p-(1-imidazolylmethyl)phenyl]-propylamine dihydrochloride as the same product in the Method A.

EXAMPLE 9

N,N-Diethyl-p-(1-imidazolylmethyl)cinnamamide

A solution of 2.64 g of p-(1-imidazolylmethyl)cinnamic acid hydrochloride, which was prepared by the Method A in Example 6, in 15 ml of thionyl chloride was refluxed for 30 minutes.

After concentration under reduced pressure, the residue was dissolved in 10 ml of dry N,N-dimethylformamide.

Then to a stirred solution of 3 ml of diethylamine and 0.1 g of 4-dimethylaminopyridine (catalyst) in 50 ml of dry dichloromethane was added the N,N-dimethylformamide solution over a period of 10 minutes at 0°-5° C., and the reaction mixture was stirred for 15 hours at room temperature.

After concentration under vacuum, the residue was dissolved in 50 ml of dichloromethane, washed with 1-2% aqueous sodium hydroxide and water, and dried over anhydrous magnesium sulfate.

The dichloromethane solution was evaporated under reduced pressure and the residual solid was recrystallized from ethanol-ether-petroleum ether to give 1.3 g of N,N-diethyl-p-(1-imidazolylmethyl)cinnamamide as pale yellow prisms; M.P. 120°-121° C.

IR-absorption spectrum (KBr): νCO: 1640 cm$^{-1}$. νC=C: 1600 cm$^{-1}$.

NMR spectrum (CDCl$_3$): δ1.05-1.4 (m, 6H), 3.50 (q, 4H), 5.13 (s, 2H), 6.80 (d, 1H), 6.88 (s, 1H), 7.08 (s, 1H), 7.13 (d, 2H), 7.49 (d, 2H), 7.53 (s, 1H), and 7.65 (d, 1H).

Elemental analysis as C$_{17}$H$_{21}$ON$_3$:

| | C (%) | H (%) | N (%) |
|---|---|---|---|
| Calcd. | 72.05 | 7.47 | 14.83 |
| Found | 71.87 | 7.60 | 14.58 |

EXAMPLE 10

3-[p-(1-Imidazolylmethyl)phenyl]propanal

To a stirred solution of 3.0 g of ethyl 3-[p-(1-imidazolylmethyl)phenyl]propionate, which was prepared by the Method I in Example 1, in 50 ml of dry toluene was added a solution of 26 ml of 20% (W/V) di-isobutyl aluminum hydride in hexane at −70° C.

over a period of 40 minutes under nitrogen atmosphere and the solution was stirred at the same temperature for 1.4 hours.

Then, 2.5 ml of methanol was added to the solution at −70° C., and the solution was warmed gradually to 0° C. over 2 hours, and 4 ml of water was added to the mixture.

After stirring at room temperature for 1 hour, the mixture was filtered and the precipitates were washed with 200 ml of ether-benzene (1:1).

The filtrate and washings were combined and dried over anhydrous magnesium sulfate.

After removal of the solvent, the residual oil was chromatographed on silica gel using chloroform to give 1.7 g of 3-[p-(1-imidazolylmethyl)phenyl]propanal as a pale yellow oil.

IR-absorption spectrum (neat): $\nu CO$: 1720 cm$^{-1}$.

NMR spectrum (CDCl$_3$): $\delta$2.6–3.1 (m, 4H), 5.06 (s, 2H), 6.88 (t, 1H), 7.03 (br-s, 1H), 7.0–7.25 (m, 4H), 7.50 (br-s, 1H), and 9.76 (t, 1H).

Elemental analysis as $C_{13}H_{14}ON_2$:

|  | C (%) | H (%) | N (%) |
|---|---|---|---|
| Calcd. | 72.87 | 6.59 | 13.08 |
| Found | 72.98 | 6.81 | 12.86 |

EXAMPLE 11 p-(1-Imidazolylmethyl)cinnamic acid

A solution of 20.0 ml of 0.1 N sodium hydroxide (2.0 mmole) was added to a solution of 529 mg (2.0 mmole) of p-(1-imidazolylmethyl)cinnamic acid hydrochloride, which was prepared by the Method A in Example 6, in 20 ml of methanol, and the reaction mixture was stirred for 1 hour at room temperature.

The solution was then concentrated under reduced pressure and the residual solid was dissolved in ethanol and the insoluble salts were filtered off. The filtrate was evaporated and the residual crystals were recrystallized from ethanol-ether to give 362 mg of p-(1-imidazolylmethyl)cinnamic acid as colorless prisms; M.P. 223°–224° C.

IR-absorption spectrum (KBr): $\nu CO$: 1680 cm$^{-1}$.

NMR spectrum (DMSO-D$_6$): $\delta$5.17 (s, 2H), and 6.3–7.8 (m, 9H).

Elemental analysis as $C_{13}H_{12}O_2N_2$:

|  | C (%) | H (%) | N (%) |
|---|---|---|---|
| Calcd. | 68.41 | 5.30 | 12.27 |
| Found | 68.36 | 5.35 | 12.15 |

FORMULATION EXAMPLE 1

10 g of p-(1-Imidazolylmethyl)cinnamic acid were admixed with 30 g of lactose, 15 g of Indian starch, 30 g of hydroxymethylcellulose, 2 g of calcium carboxymethylcellulose and 1 g of calcium stearate. The mixture was kneaded and shaped into 1,000 tablets.

FORMULATION EXAMPLE 2

The tablets obtained in Formulation Example 1 were placed in a rotary coating tank and a 10% ethanolic solution of 1 g of polyvinylacetal diethylaminoacetate and 0.3 g of macrogol 6000 was added to the tablets and the mixture was stirred and dried.

FORMULATION EXAMPLE 3

5 g of p-(1-Imidazolylmethyl)cinnamic acid and 10 g of chlorobutanol were dissolved in distilled water for injection to make the total amount 1,000 ml. 1 ml of the solution was poured into an ampoule to make 1,000 ampoules. The air was purged with nitrogen, and the ampoules were heated at 121° C. for 15 minutes to sterilize the solution to obtain injectable preparation.

While the invention has been described in detail and with reference to specific embodiments thereof, it will be apparent to one skilled in the art that various changes and modifications can be made therein without departing from the spirit and scope thereof.

What is claimed is:

1. A compound of the formula:

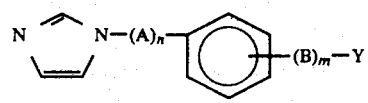

wherein Y is a carboxyl group or an alkoxycarbonyl group having 2 to 7 carbon atoms, A and B, which may be the same or different, each is a straight- or branched-chain alkylene or alkenylene group having 1 to 8 carbon atoms, n and m are zero or 1, with the proviso that the aggregate number of the linear carbon atoms in A and B is 2, 3 or 4; and the pharmaceutically acceptable salts thereof.

2. A compound as claimed in claim 1 of the formula:

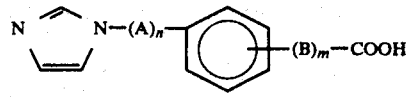

wherein A, n, B and m have the same meanings as in claim 1.

3. A compound as claimed in claim 1 of the formula:

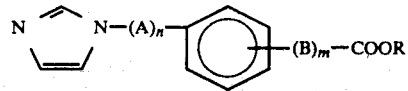

wherein R is a straight- or branched-chain alkyl group having 1 to 6 carbon atoms, A, n, B and m have the same meanings as in claim 1.

4. The compound as claimed in claim 2 of the formula:

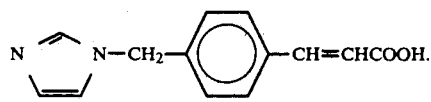

5. The compound as caimed in claim 2 of the formula:

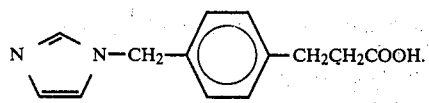

6. The compound as claimed in claim 2 of the formula:

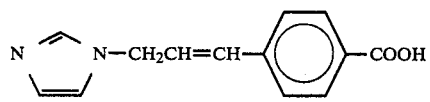

7. The compound as caimed in claim 2 of the formula:

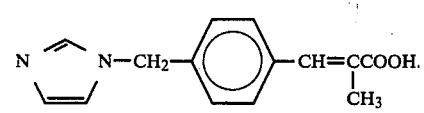

8. The compound as claimed in claim 2 of the formula:

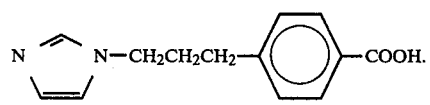

9. The compound as claimed in claim 2 of the formula:

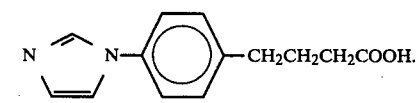

10. The compound as claimed in claim 2 of the formula:

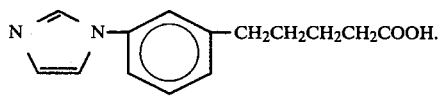

11. The compound as claimed in claim 2 of the formula:

12. The compound as claimed in claim 3 of the formula:

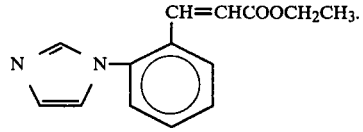

13. The compound as claimed in claim 3 of the formula:

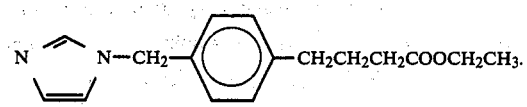

14. The compound as claimed in claim 3 of the formula:

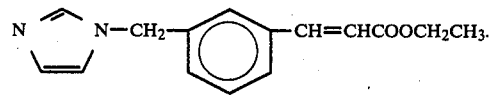

15. The compound as claimed in claim 3 of the formula:

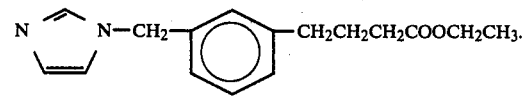

16. The compound as claimed in claim 3 of the formula:

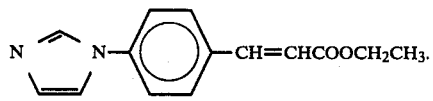

17. The compound as claimed in claim 3 of the formula:

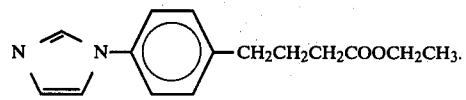

18. The compound as claimed in claim 3 of the formula:

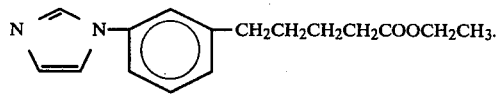

19. The compound as claimed in claim 3 of the formula:

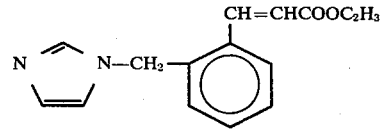

20. A pharmaceutical composition for alleviating diseases caused by thromboxane $A_2$ in mammals for oral administration containing, as an active ingredient, a compound of claim 1 in an amount in the range of about 1 to about 1000 mg per day per body in combination with a pharmaceutically acceptable carrier or diluent.

21. A pharmaceutical composition for alleviating diseases caused by thromboxane $A_2$ in mammals for parenteral administration containing, as an active ingredient, a compound of claim 1 in an amount in the range of about 0.1 to about 100 mg per day per body in combination with a pharmaceutically acceptable carrier or diluent.

22. A method of alleviating the diseases caused by thromboxane $A_2$ in mammals which comprises administering a therapeutically effective amount of a compound of claim 1.

* * * * *